United States Patent [19]
Parodi

[11] Patent Number: 5,820,595
[45] Date of Patent: Oct. 13, 1998

[54] ADJUSTABLE INFLATABLE CATHETER AND METHOD FOR ADJUSTING THE RELATIVE POSITION OF MULTIPLE INFLATABLE PORTIONS OF A CATHETER WITHIN A BODY PASSAGEWAY

[76] Inventor: Juan C. Parodi, Mercedes 4255, Buenos Aires, Argentina, 1419

[21] Appl. No.: 475,755

[22] Filed: Jun. 7, 1995

[51] Int. Cl.⁶ .................................................. A61M 5/00
[52] U.S. Cl. ............................................. 604/101; 604/96
[58] Field of Search ........................... 604/101, 96, 104; 606/194; 623/12.1

[56] References Cited

U.S. PATENT DOCUMENTS

| | | | |
|---|---|---|---|
| 4,105,022 | 8/1978 | Antoskin et al. | 128/2.05 |
| 4,295,164 | 10/1981 | Shihata | 128/1 R |
| 4,577,631 | 3/1986 | Kreamer | 128/334 |
| 4,655,746 | 4/1987 | Daniels et al. | 604/53 |
| 5,219,355 | 6/1993 | Parodi et al. | 606/191 |
| 5,342,306 | 8/1994 | Don Michael | 604/101 |
| 5,360,443 | 11/1994 | Barone et al. | 623/1 |

FOREIGN PATENT DOCUMENTS

| | | |
|---|---|---|
| 2647681 | 12/1990 | France . |
| 5735985 | 7/1982 | Japan . |
| WO8707510 | 6/1987 | WIPO . |
| WO9516487 | 12/1994 | WIPO . |

*Primary Examiner*—Wynn Wood Coggins
*Assistant Examiner*—N. Kent Gring
*Attorney, Agent, or Firm*—Tobor & Goldstein, L.L.P.

[57] ABSTRACT

An adjustable inflatable catheter having a shaft, two or more inflatable portions disposed on the shaft and means for adjusting the position of at least one of the inflatable portions relative to the shaft while the catheter is disposed within a body passageway, and a method for adjusting the position of at least one inflatable portion of a catheter relative another inflatable portion of the catheter while the catheter is located in a body passageway.

34 Claims, 5 Drawing Sheets

ADJUSTABLE INFLATABLE CATHETER AND METHOD FOR ADJUSTING THE RELATIVE POSITION OF MULTIPLE INFLATABLE PORTIONS OF A CATHETER WITHIN A BODY PASSAGEWAY

BACKGROUND OF THE INVENTION

1. Field of the Invention

The invention relates to an adjustable catheter having multiple inflatable portions, and a method for varying the position of at least one inflatable portion of a catheter with respect to another inflatable portion of the catheter while the catheter is in a body passageway.

2. Description of the Prior Art

Various types of surgical procedures for repairing and reinforcing, or dilating and expanding body passageways require the use of catheters. It is well known that catheters having inflatable portions, or balloons, are used to expand body passageways such as arteries and ureters, for the removal of blockages or other surgical procedures. Balloon catheters are also used to implant prostheses, or grafts, in arteries, ureters and other body passageways. For such implanting, the inflatable portion, or balloon, of a catheter is used to expand and deform an attachment device or securing means, disposed on the balloon and associated with the prosthesis, by subjecting the attachment device or securing means to expansion forces by inflation of the balloon. Upon deflation of the balloon and removal of the catheter, the attachment device and prosthesis remain anchored to the internal wall of the body passageway.

The use of catheters with multiple inflatable balloons is known in the prior art. Such prior art multi-balloon catheters are limited by the feature of having a fixed distance between the catheter balloons. A significant disadvantage of the prior art multi-balloon catheter is the inability to adjust the distance between the balloons while the catheter is in the body passageway.

A conventional procedure is known for viewing the position of catheter balloons while the catheter is disposed in a body passageway, such as with an x-ray device or fluoroscope. When the balloon portions of prior art catheters are located in the body passageway, the predetermined, fixed distance between the catheter balloons may not reflect the ideal, or desired, distance determined while the catheter is viewed in the body passageway between the attachment devices carried on the balloons. When that occurs, either the catheter must be completely removed from the body passageway and the distance between the balloons readjusted or the catheter replaced with a catheter having a predetermined distance between inflatable portions that more closely matches the desired distance; or the attachment devices and prosthesis may be implanted without accurate spacing.

Accordingly, prior to the development of the present invention, there has been no intraluminally adjustable multi-balloon catheter or method for adjusting the distance between balloons of a multi-balloon catheter, which: allows for the adjustment and precise placement of multiple balloons, attachment devices and prosthesis in the body passageway while the catheter is in the body passageway; minimizes surgery time and is cost effective; and does not require removal of the catheter for adjustment of the distance between multiple balloons. Therefore, the art has sought a multi-balloon catheter and method for adjusting the distance between multiple balloons of a multi-balloon catheter which are believed to: be time and cost efficient; provide precise adjustment and placement of multiple balloons and attachment devices to secure a prosthesis within a body passageway; and not require the removal of the catheter for adjustment of the distance between balloons.

SUMMARY OF THE INVENTION

In accordance with the invention, the foregoing advantages have been achieved through the present adjustable inflatable catheter. The present invention includes a catheter for insertion into a body passageway, including: a shaft having first and second ends and a longitudinal axis extending therebetween; first and second inflatable members disposed on the shaft along the longitudinal axis of the shaft; and means for adjusting the position of at least one of the first and second inflatable members along the longitudinal axis of the shaft while the catheter is disposed within the body passageway.

The feature of the present invention is that the shaft may include a first passage disposed in fluid transmitting relationship with the first inflatable member to allow the first inflatable member to be expanded upon the introduction of a fluid into the first passage. In addition, the first and second inflatable members may be first and second inflatable balloons.

A further feature of the present invention is that the adjusting means may be first and second moveable members that are: disposed on the shaft between the first inflatable member and the second end of the shaft; associated with each other by a connection means to allow their cooperative movement along the longitudinal axis of the shaft; and which carry the second inflatable member attached to the first moveable member at its first end and to the second moveable member at its second end. The first and second moveable members may be spaced from each other to form an annular clearance disposed between the first and second moveable members, the annular clearance being in fluid transmitting relationship with the second inflatable member so that the second inflatable member may be expanded upon the introduction of fluid into the annular clearance.

The adjusting means of the present invention may take the form of an alternate embodiment that includes a single moveable member that: is disposed upon the shaft of the catheter for movement along the longitudinal axis of the shaft; carries the second inflatable member; includes a second passage disposed in fluid transmitting relationship with the second inflatable member to allow the second inflatable member to be expanded upon the introduction of a fluid into the second passage; and is moveable with respect to the first inflatable member.

In accordance with the present invention, the foregoing advantages have also been achieved by an apparatus for repairing a body passageway. This aspect of the present invention may include: a catheter, having first and second inflatable members disposed upon its shaft along the longitudinal axis of the shaft; a first securing means disposed upon the first inflatable member; a second securing means disposed upon the second inflatable member; a prosthesis having first and second ends, whereby the first securing means is attached to the prosthesis proximate the first end of the prosthesis and the second securing means is associated with the prosthesis proximate the second end of the prosthesis; and means for adjusting the location of the second inflatable member with respect to the first inflatable member along the longitudinal axis of the shaft. A further feature of the present invention is that the first and second securing means may be expandable tubular shaped members.

In accordance with the invention, the foregoing advantages have also been achieved through the present method for adjusting the position of at least one of the inflatable portions of a catheter while the catheter is located in a body passageway. The method of the present invention may include the steps of: disposing the catheter in the body passageway; positioning the first inflatable member of the catheter in the body passageway at a desired location; and moving the moveable means of the catheter relative the shaft of the catheter along the longitudinal axis of the shaft to selectively position the second inflatable portion of the catheter with respect to the first inflatable portion.

Another aspect of the present invention is a method for adjusting the position of at least one of the inflatable portions of a catheter while the catheter is located in the body passageway to implant, within the body passageway, a prosthesis carried upon the catheter. This aspect of the present invention may include the steps of: providing a first securing means for the first end of the prosthesis; providing the first securing means and the first end of the prosthesis on the first inflatable portion of the catheter; providing a second securing means on the second inflatable portion of the catheter; disposing the catheter, first securing means and prosthesis within the body passageway; positioning the first inflatable portion of the catheter, first securing means and first end of the prosthesis within the body passageway at a desired location; and moving the second inflatable portion of the catheter with respect to the first inflatable portion.

A further feature of this aspect of the present invention may include the steps of inflating the first inflatable portion to expand the first securing means, causing the first securing means and first end of the prosthesis to be secured within the body passageway. This aspect of the present invention may include the further steps of positioning the second inflatable portion of the catheter at a desired location within the prosthesis and inflating the second inflatable portion to expand the second securing means, securing the second securing means and prosthesis within the body passageway. An additional feature of the present method may include the steps of: providing at least one moveable member disposed on the catheter; disposing the second inflatable portion of the catheter onto the at least one moveable member; and positioning the second inflatable portion at a desired location within the body passageway by moving the at least one moveable member relative the first inflatable portion of the catheter after the first inflatable portion is positioned within the body passageway. A final feature of this aspect of the present invention may include the further steps of inflating the second inflatable member to expand the second securing means and secure the second securing means and prosthesis within the body passageway, deflating the first inflatable member, deflating the second inflatable member, and removing the catheter from the body passageway.

The adjustable inflatable catheter and method for adjusting the relative position of multiple inflatable portions of a catheter within a body passageway of the present invention, when compared with previously proposed prior art devices and methods, are believed to have the advantages of: being time and cost efficient; providing precise adjustment and placement of multiple balloons and attachment devices to secure a prosthesis to a body passageway; and not requiring the removal of the catheter for adjustment of the distance between adjacent balloons of a multi-balloon catheter.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1:
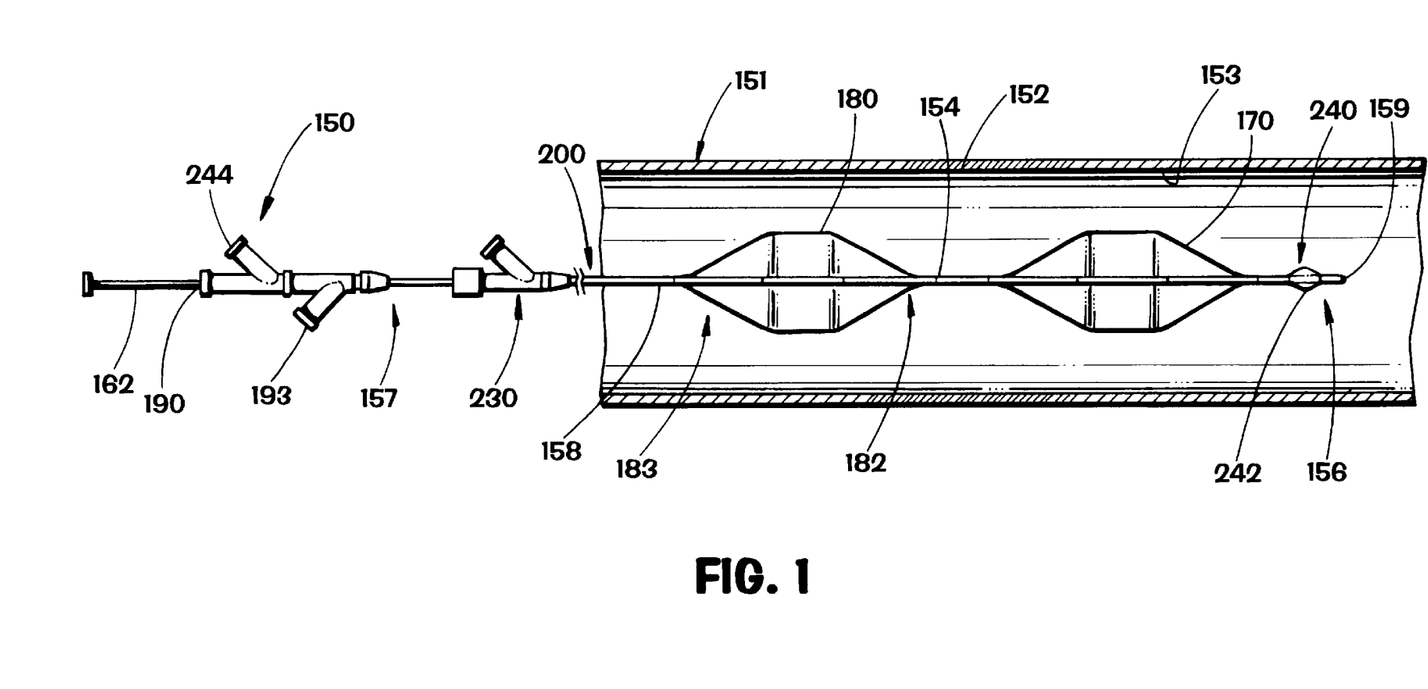
FIG. 1 is a partial cross-sectional view along the longitudinal axis of the catheter of the present invention disposed in a body passageway.
Figure 2:
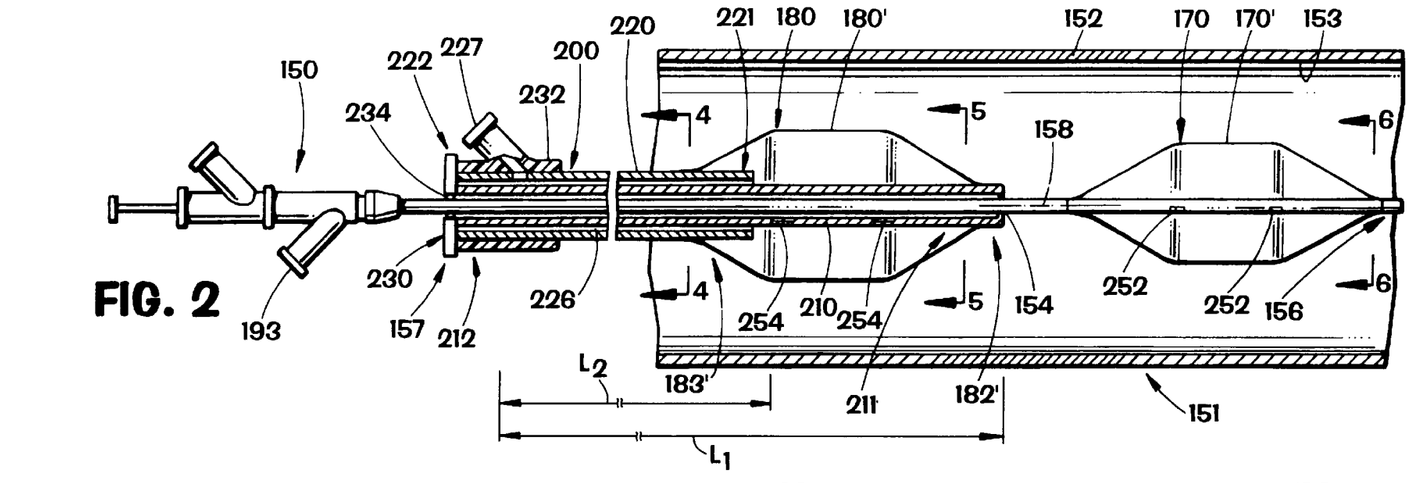
FIG. 2 is a partial cross-sectional view of a first preferred embodiment of the catheter of the present invention disposed in a body passageway.
Figure 3:
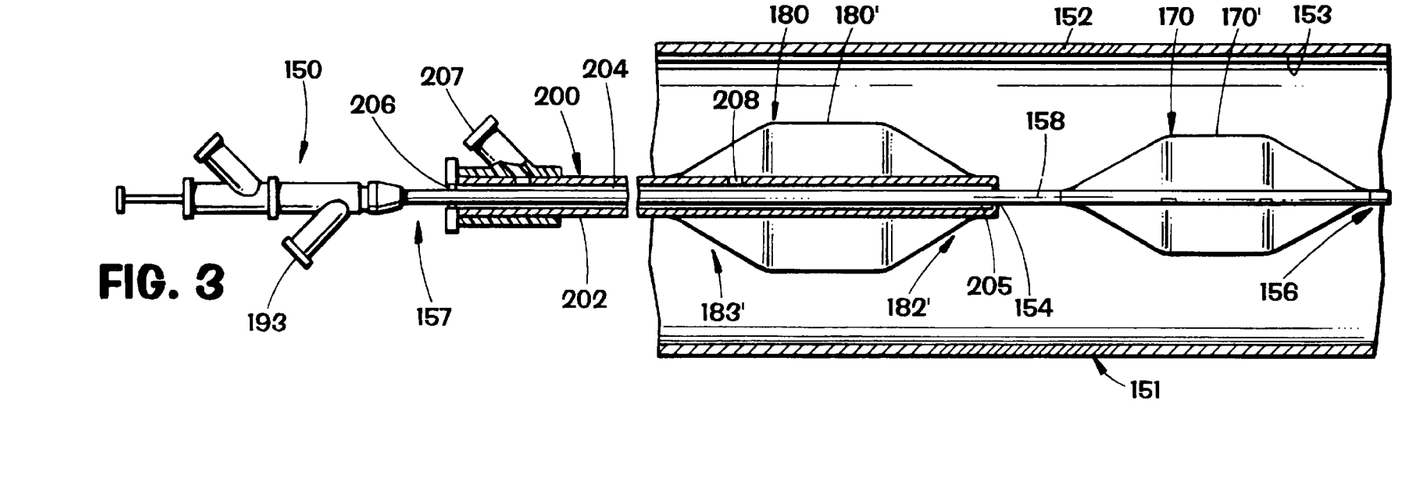
FIG. 3 is a partial cross-sectional view of a second preferred embodiment of the catheter of the present invention disposed in a body passageway.

FIGS. 1–3 illustrate a catheter 150 for expanding a body passageway 151 or implanting a prosthesis, or graft, (350, FIG. 9) in the body passageway 151 at a desired location 152. Generally, catheter 150 includes a shaft 154 having first and second ends 156, 157, respectively, and a longitudinal axis 158 extending therebetween. The first end 156 of the shaft 154, is located at the distal end of the catheter and is to be inserted into the body passageway 151 and the second end 157 of the shaft 154 is located at the proximal end of the catheter 150.

Any number of inflatable members may be disposed upon the shaft 154. For purposes of illustration, shaft 154 is shown in FIGS. 1–3 to have first and second inflatable members 170 and 180, respectively, disposed about its longitudinal axis 158. The inflatable members 170, 180 may be of any known type of inflatable member suitable for use in connection with catheters, such as balloons 170', 180' (FIGS. 2 and 3). The inflatable members 170, 180, or balloons 170', 180', may be of any shape, as long as they have the requisite strength and flexibility to be inflated and deflated, and are capable of expanding and deforming a means for securing a prosthesis within a body passageway as will be hereinafter described in further detail. In the preferred embodiment, the first inflatable member 170, or balloon 170', is disposed upon the shaft 154 proximate the first end 156 of the shaft 154. The second inflatable member 180, or balloon 180', having first and second ends 182, 183 and 182', 183', respectively, is disposed upon the shaft 154 between the first inflatable member 170, or balloon 170', and the second end 157 of the shaft 154.

Figure 4:
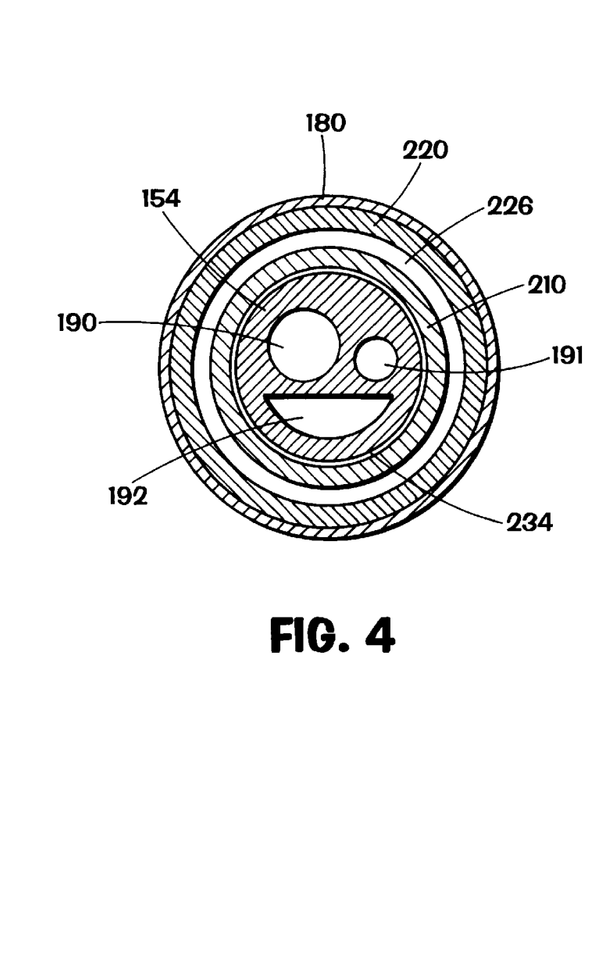
FIG. 4 is an enlarged cross-sectional view of the catheter of FIG. 2, taken along line 4—4 of FIG. 2.
Figure 5:
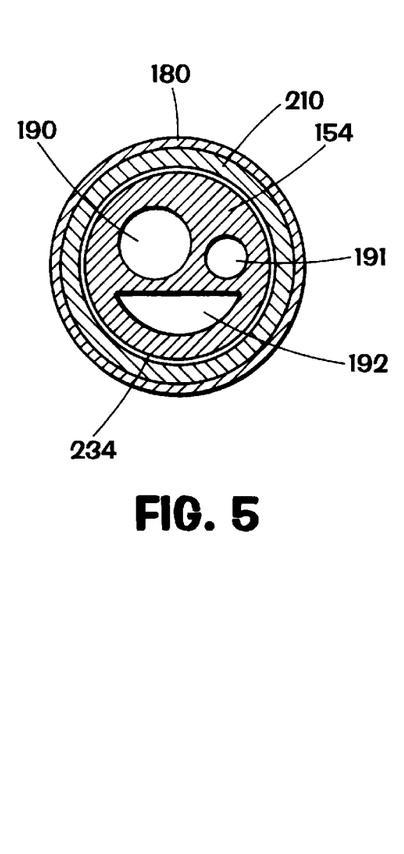
FIG. 5 is an enlarged cross-sectional view of the catheter of FIG. 2, taken along line 5—5 of FIG. 2.
Figure 6:
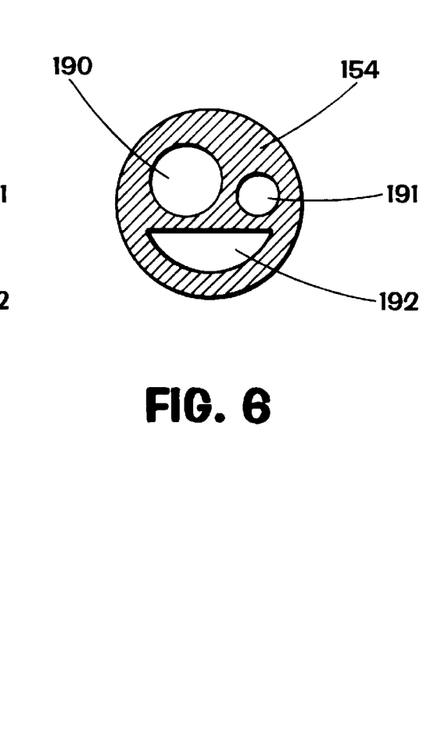
FIG. 6 is an enlarged cross-sectional view of the catheter of FIG. 2, taken along line 6—6 of FIG. 2.

The shaft 154 of catheter 150 may include a plurality of internal passages. For example, FIGS. 4–6 illustrate shaft 154 having three internal passages 190, 191 and 192, each extending through the shaft 154 along the longitudinal axis 158 of the shaft 154. One of the plurality of internal passages of the shaft 154 may be utilized to provide a passage, or lumen, for a conventional guide wire, or mandrel. For example, FIG. 1 illustrates guide wire 162 extending through the passage 190 (FIGS. 4–6) of the shaft 154. The guide wire 162 is preferably of standard construction and may exit the shaft 154 through a conventional nosepiece 159.

Another passage among the plurality of internal passages of the shaft 154 may be used to allow the introduction of a fluid into one of the inflatable members disposed on the shaft 154 from an outside source through an inlet port associated with the shaft 154 to allow such inflatable member to be selectively inflated and deflated. Each inflatable member may thus each be disposed on the shaft 154 in fluid transmitting relationship with at least one internal passage of the shaft 154. For example, the first inflatable member 170 or balloon 170' may be disposed in fluid communication with internal passage 191 (FIG. 4), which is in fluid communication with an inlet port 193 (FIG. 1). A suitable fluid may be provided into the inlet port 193 in a conventional manner from an outside source (not shown).

The catheter 150 includes means for adjusting the position of at least one of the plurality of inflatable members along the longitudinal axis 158 of the shaft 154 relative the shaft 154 while the catheter 150 is disposed in the body passageway 151. In the preferred embodiment of FIG. 1, the catheter 150 includes means for adjusting 200 the position of the second inflatable member 180 relative to the shaft 154 and first inflatable member 170 along the longitudinal axis 158 of the shaft 154.

FIGS. 2 and 4–6 illustrates a preferred embodiment of the means for adjusting 200 the position of the second inflatable member 180, or balloon 180', which includes first and second moveable tubular members 210 and 220. The first moveable member 210 has first and second ends 211 and 212, respectively, and the second moveable member 220 has first and second ends 221 and 222, respectively. The first moveable member 210 has a friction fit upon shaft 154, whereby the internal diameter of first moveable member 210 closely conforms, in a sealing relationship, with the outer wall surface of shaft 154. The first and second movable members 210, 220 may be associated in a manner which allows their cooperative movement with respect to the shaft 154 along the longitudinal axis 158 of the shaft 154. For example, the moveable members 210, 220 may be associated proximate their second ends 212, 222, by connection means 230, which connects the first and second moveable member 210, 220 to each other. In FIG. 2, the connection means 230 is illustrated by a Y-connector 232, which connects first and second moveable members 210, 220 proximate their respective second ends 212, 222 and includes an annulus 234 through which the shaft 154 passes to allow cooperative, slidable, movement of the Y-connector 232 and moveable members 210, 220 over the shaft 154 along its longitudinal axis 158.

In the preferred embodiment of FIG. 2, and as seen in FIGS. 4 and 5, the second inflatable member 180, or balloon 180', is secured to the means for adjusting 200 the position of the second inflatable member 180, or balloon 180', to allow the second inflatable member 180, or balloon 180', to be moveable relative the first inflatable member 170, or balloon 170', along the longitudinal axis 158 of the shaft 154. For example, the first end 182' of the second balloon 180' may be secured to the first moveable member 210 proximate its first end 211 and the second end 183' of the second balloon 180' may be secured to the second movable member 220 proximate its first end 221. Thus, upon movement of the first and second moveable members 210, 220, the location of the second inflatable member 180, or balloon 180', may be adjusted with respect to the first inflatable member 170 or balloon 170'.

An annular clearance may be provided in connection with the first and second moveable members 210, 220 to allow the introduction of a fluid into the second inflatable member 180, or balloon 180'. FIGS. 2 and 4 illustrate an annular clearance 226 formed between the first and second movable members 210, 220. Fluid may be introduced into the annular clearance 226 through an inlet port 227. In the embodiment of FIG. 2, the annular clearance 226 opens into the second inflatable member 180 or balloon 180' as a result of the length $L_1$ of the first moveable member 210 being greater than the length $L_2$ of the second movable member 220, allowing the annular clearance 226 to be in fluid communicating relationship with the second balloon 180'.

Thus, upon controlled movement of the connection means 200 from outside the body, which in turn simultaneously moves the first and second moveable tubular members 210, 220, the location of the second inflatable member 180, or balloon 180', with respect to the first inflatable member 170, or balloon 170', may be adjusted along the longitudinal axis 158 of the shaft 154. The inflatable members 170, 180, or balloons 170', 180', may be expanded upon the introduction of a fluid into entry ports 193, 227 and through passage 191 (FIG. 5) and clearance 226, respectively, in a conventional manner.

FIG. 3 illustrates an alternate embodiment of the means for adjusting 200, which includes a single moveable tubular member 202, upon which the second inflatable member 180, or balloon 180' is disposed. Moveable member 202 is slidably moveable upon the shaft 154 along the longitudinal axis 158 of the shaft 154 relative to the shaft 154 and first inflatable member 170, or balloon 170'. The moveable member 202 is disposed about, and has a friction fit about, the shaft 154, as previously described in connection with FIG. 2. The moveable member 202 may include a passage for the introduction of fluid into the second balloon 180' for inflation and deflation of the second balloon 180'. For example, FIG. 2 illustrates a passage 204 formed between the moveable member 202 and shaft 154, seals 205 and 206 at each end of the moveable member 202, and fluid entry and exit ports, 207 and 208, respectively, for the introduction of fluid into the passage 204 and second balloon 180' from an outside source.

Radiopaque markers may be attached to the catheter 150 at predetermined, select locations to allow the location of the catheter 150 and the inflatable members 170, 180 to be monitored with the use of a fluoroscope or x-ray device while the catheter 150 is in the body passageway 151. For example, FIG. 3 illustrates the use of a first pair of radiopaque markers 252 disposed on the shaft 154 proximate the first balloon 170' and a second pair of radiopaque markers 254 disposed on the first movable member 210 proximate the second balloon 180' for monitoring the position of the first and second balloons 170', 180' in the body passageway 151.

Figure 7:
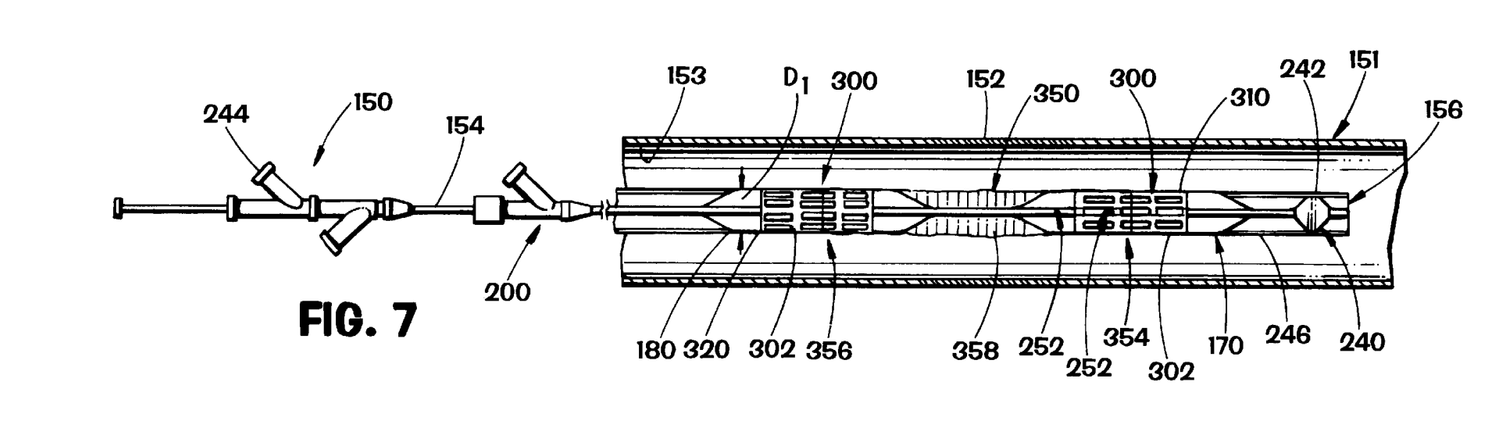
FIG. 7 is a partial cross-sectional view of the catheter of the present invention, including a prosthesis, or graft, and securing means, disposed in a body passageway.
Figure 8:
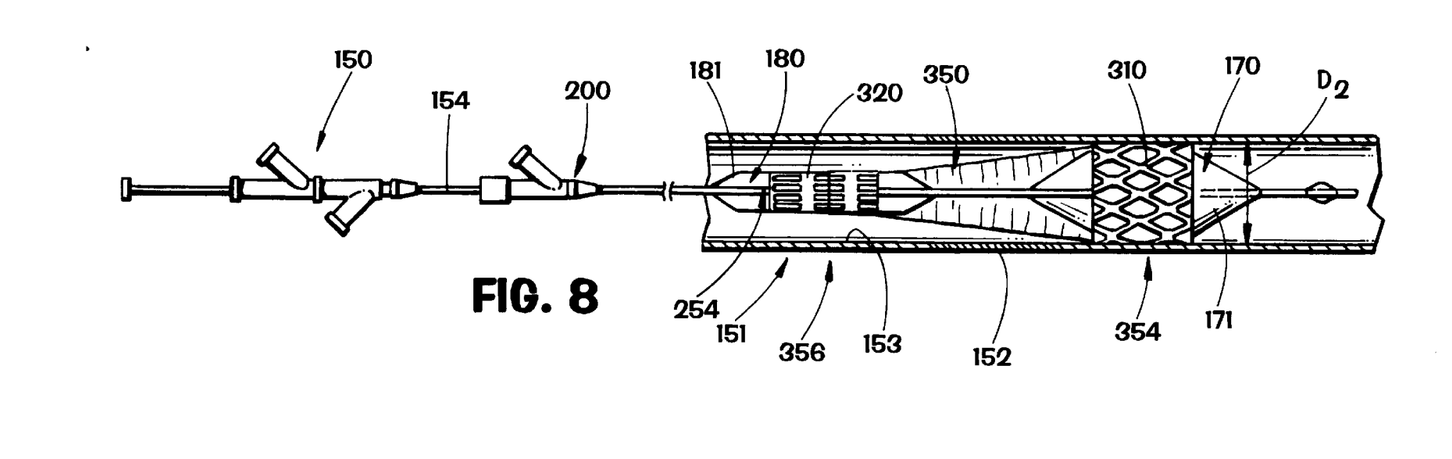
FIG. 8 is a partial cross-sectional view of the catheter of the present invention, including a prosthesis, or graft, and securing means, and illustrating a first inflatable portion of the catheter in an inflated configuration disposed in a body passageway.
Figure 9:
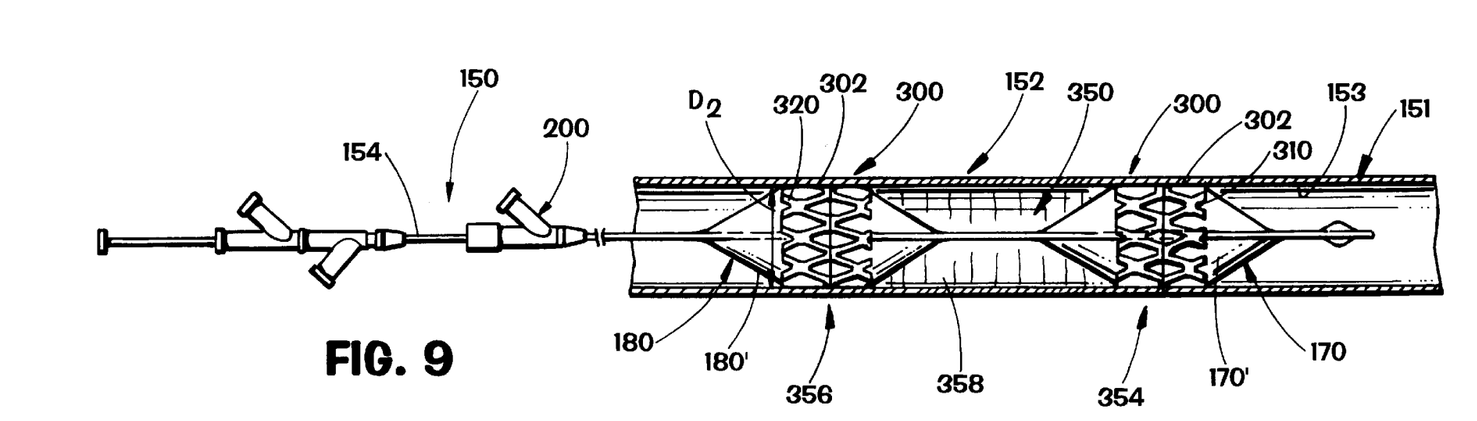
FIG. 9 is a partial cross-sectional view of the catheter of the present invention, including a prosthesis, or graft, and securing means, and illustrating first and second inflatable portions of the catheter in an inflated configuration disposed in a body passageway.

As shown in FIGS. 7–9, the catheter 150 of the present invention may include a prosthesis, or graft, 350 and means for securing 300 the prosthesis 350 within the body passageway 151. As will be hereinafter described in further detail, a securing means 300 is preferably attached to each end of the prosthesis 350 and is preferably disposed on at least one inflatable member of the catheter 150 for delivery into the body passageway 151, and to anchor the prosthesis 350 to the interior wall 153 of the body passageway 151. After the securing means 300 and prosthesis 350 are released from the catheter 150, the prosthesis 350 provides a passageway 360 (FIG. 10) through the body passageway 151 so that the body fluid flowing through the body passageway 151 can pass through the location of the prosthesis 350, such as a location 152 of repair or reinforcement.

With further reference to FIGS. 7–9, the prosthesis 350 may be a tubular graft having first and second ends 354, 356 and a flexible wall 358 disposed therebetween, the graft 350 adapted to be disposed within the body passageway 151, such as the graft described in U.S. Pat. No. 5,360,443, issued Nov. 1, 1994, and incorporated herein by reference. Each securing means 300 may be at least one expandable tubular shaped member 302. Any known type of intraluminally deliverable expandable member 302 could be utilized as securing means 300 provided it has the ability to be secured to a prosthesis and carried on an inflatable member of a catheter and expanded from a first diameter $D_1$, which permits intraluminal delivery of the expandable member 302, to a second expanded $D_2$, in order to secure the expandable member 302 and prosthesis 350 to the interior wall 153 of the body passageway 151 (FIGS. 7 and 8). An example of an expandable tubular shaped member 302 suitable for use in the present invention is shown in U.S. Pat. No. 4,773,665, issued Mar. 29, 1988, incorporated herein by reference.

FIG. 8 illustrates a prosthesis, or graft, 350 and first securing means 310 associated with the first end 354 of the graft 350 and releasably mounted onto the first inflatable member 170 and a second securing means 320 associated with the second end 356 of the graft 350 and releasably mounted onto the second inflatable member 180 for delivery into the body passageway 151. The first and second securing means 310, 320 may be associated with the first and second ends 354, 356 of the prosthesis 350 in any suitable manner, such as by small sutures. Further, the second securing means 320 may be releasably mounted on the second inflatable member 180 without being attached to the prosthesis 350, such that the second securing means 320 becomes associated with the prosthesis 350 at a desired location within the prosthesis 350 when the second inflatable member 180 is inflated. The securing means 300 may be releasably mounted upon the inflatable members 170, 180 of catheter 150 in any suitable fashion, whereby upon inflation of the inflatable members 170, 180, the securing means 300 is forced radially outwardly into contact with the interior wall 153 of the body passageway 151 and the interior wall of the prosthesis, or graft, 350.

The prosthesis 350 and securing means 300 are disposed on the catheter 150 by passing the catheter 150 through the prosthesis 350 and securing means 300, such that the securing means 300 are disposed on the inflatable members 170, 180 of the catheter 150 and the prosthesis 350 extends therebetween. The catheter 150, as illustrated in FIG. 7, is in the configuration it would have for intraluminal delivery. The first and second securing means 310, 320 have their first unexpanded, undeformed diameter $D_1$, and first and second inflatable members 170, 180 are shown completely deflated. When catheter 150 is being intraluminally delivered, catheter 150, first and second securing means 310, 320, and prosthesis 350 are preferably enclosed by a conventional delivery sheath 246 (FIG. 7), which is removed as catheter 150 is disposed at the desired location within the body passageway 151. As shown in FIGS. 1 and 7, a third inflatable member 240 or balloon tip 252 may be disposed on the shaft 154 between the first inflatable member 170 and the first end 156 of the shaft 154 for sealing the end of the delivery sheath 246 to prevent body fluid from entering the sheath 246 and disturbing the integrity and positioning of the first and second inflatable members 170, 180, prosthesis 350 and securing means 300. The third inflatable member 240, or balloon tip 242 may be in fluid communication with one of the passages of the shaft 154, such as passage 192 (FIGS. 4–6) which is in fluid communication with inlet port 244 for inflation and deflation of the balloon tip 242.

Figure 10:
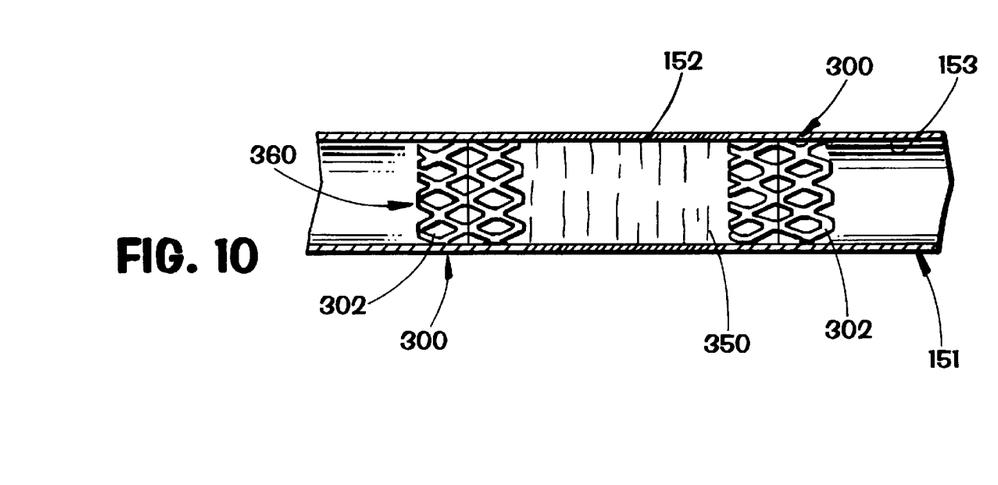
FIG. 10 is a partial cross-sectional view of a body passageway with a prosthesis and securing means secured therein.

FIGS. 8–10 illustrate catheter 150 in use for implanting a prosthesis 350 in a body passageway 151. The catheter 150, prosthesis 350 and securing means 300 may be intraluminally delivered to the desired location 152 within the body passageway 151 and the sheath 246 withdrawn in a conventional manner. As the inflatable portions 170, 180 are expanded to expand the securing means 300 to a desired diameter, the prosthesis 350 opens and has a diameter substantially equal to the diameter $D_2$ of the securing means 300, as shown in FIGS. 8 and 9. Expansion and deformation of the first and second securing means 310, 320 is accomplished by the expansion of first and second inflatable members 170, 180 of catheter 150, in a conventional manner. Such expansion of the inflatable members 170, 180 may be accomplished independently or simultaneously or independently as desired and controlled by an operator.

FIG. 8 illustrates first inflatable member 170 inflated and first securing means 310 in its expanded configuration having diameter $D_2$. First securing means 310 and the first end 354 of prosthesis 350 are shown urged against the interior wall 153 of the body passageway 151. FIG. 9 illustrates both first and second inflatable members 170, 180 inflated and first and second securing means 310, 320 in an expanded configuration having diameters $D_2$. Deflation of inflatable members 170, 180 permits release of the inflatable members 170, 180 and catheter 150 from the body passageway 151 and prosthesis 350, after the prosthesis 350 and first and second securing means 310, 320 have been expanded and anchored to the interior wall 153 of the body passageway 151. After withdrawal of the catheter 150 from the body passageway 151, the body passageway 151, graft 350, and securing means 300, have the configuration shown in FIG. 10.

The catheter 150 of the present invention may similarly be used without a prosthesis and securing means for other purposes. A method, for use with a catheter 150 having at least first and second inflatable portions 170, 180, for adjusting the position of at least one of the inflatable portions while the catheter 150 is located in a body passageway 151 will now be described. The catheter 150, as described with respect to FIGS. 1–3 above, includes a shaft 154, and moveable means 200 disposed on the shaft 154 for relative movement along the longitudinal axis 158 of the shaft 154. The first inflatable portion 170 is disposed on the shaft 154 and the second inflatable portion 180 is disposed on moveable means 200. The catheter 150 is disposed in the body passageway 151. The first inflatable member 170 is then positioned in the body passageway 151 at a desired location by controllably moving the catheter 150. The second inflatable portion 180 may be selectively positioned with respect to the first inflatable portion 170 by moving the moveable means 200 relative the shaft 154 along the longitudinal axis 158 of the shaft 154. The first and second inflatable portions 170, 180 may be controllably inflated, as previously described, in order to urge the inflatable portions 170, 180 against the interior wall 153 of the body passageway 151.

With reference to FIGS. 7–10, a method for adjusting the position of at least one inflatable portion of a catheter 150, having at least two inflatable portions, while the catheter 150 is disposed in a body passageway 151 to implant a prosthesis 350 carried on the catheter 150 will be described. The catheter 150, as described above with reference to FIGS. 1–6, would initially have first and second inflatable members 170, 180 or balloons 170', 180' uninflated, with the inflatable members 170, 180 or balloons 170', 180' disposed with respect to catheter 150 in a conventional manner to permit intraluminal delivery of the catheter 150 (FIG. 7). A first securing means 310, as previously described, would be associated with first inflatable member 170, and a second securing means 320 would be associated with the second inflatable member 180. The prosthesis 350 could be attached at its ends to the securing means 310, 320 and extend therebetween, or be attached only at its first end 354 to first securing means 310. The delivery sheath 246 would then be disposed about catheter 150, and the catheter 150 delivered into the body passageway 151. Thereafter, the delivery sheath 246 is withdrawn in a conventional manner.

With a conventional intraluminal imaging technique, such as with the use of a fluoroscope or x-ray device, to view the radiopaque marker or markers 252 disposed in the proximity of the first inflatable member 170, the first inflatable member 170, upon which the first securing means 310 and first end 354 of the prosthesis 350 is disposed, may be positioned at the desired location in the body passageway 151. As shown in FIG. 8, the first inflatable member 170 may be controllably inflated, as previously described, to expand the first securing means 310 and anchor the first securing means 310 and first end 354 of the prosthesis 350 to the interior wall 153 of the body passageway 151.

Thereafter, the second inflatable member 180, second securing means 320, and second end 356 of the prosthesis 350 (if the second securing means 320 is attached to the second end 356 of the prosthesis 350 prior to delivery), may be selectively positioned in the body passageway 151 relative the first inflatable member 170 by moving the means for adjusting 200, the position of the second inflatable member 180 relative the shaft 154. The use of a similar imaging technique as described above would allow the location of the radiopaque members 254 and second inflatable member 180 to be viewed. If the second securing means 320 is attached to the prosthesis 350, the prosthesis 350 will stretch sufficiently to allow its cooperative movement with the second securing means 320, as the second inflatable member 180 is moved. Otherwise, the second inflatable member 180 will be moved within the prosthesis 350 along the longitudinal axis 156 of the shaft 154. The second inflatable member 180 may be inflated to expand the second securing means 320 and anchor the second securing means 320 and prosthesis 350 against the interior wall 153 of the body passageway 151 (FIG. 9). As previously described, the inflatable members 170, 180 may be inflated and deflated simultaneously or independently as desired. As shown in FIG. 10, the first and second securing means 310, 320 and prosthesis 350 will remain anchored within the body passageway 151 after the first and second inflatable members 170, 180 are deflated and the catheter 150 is removed from the body passageway 151. The catheter 150 of the present invention thus allows the selective and precise positioning of the second securing means 320 and second end 356 of the prosthesis 350 within the body passageway 151 relative to the position of the first securing means 310 and first end 354 of the prosthesis 350.

The catheter 150 of the present invention and method of positioning multiple inflatable portions of the catheter 150 in the body passageway 151 are believed to be useful to expand, repair or reinforce numerous types of body passageways including abdominal aortic aneurysms, arterial venous fistulas, false aneurysms, dissection procedures, trauma-injury of arteries, and ureters, as well as to provide internal bypasses.

It is to be understood that the invention is not limited to the exact details of construction, operation, exact materials or embodiments shown and described, as obvious modifications and equivalents will be apparent to one skilled in the art. For example, the catheter could be provided with three inflatable portions, at least one of which may be moveable relative the other inflatable portions. Accordingly, the invention is therefore to be limited only by the scope of the appended claims.

I claim:

1. A catheter for insertion into a body passageway, comprising:

a shaft, having first and second ends and a longitudinal axis extending from the first end to the second end of the shaft;

first and second inflatable members disposed on the shaft along the longitudinal axis of the shaft;

means for inflating the first and second inflatable members; and means for adjusting the position of at least one of the first and second inflatable members relative to the shaft along the longitudinal axis of the shaft while the catheter is disposed within the body passageway, the adjusting means including first and second movable members disposed on the shaft between the first inflatable member and the second end of the shaft, and the first and second movable members are spaced from each other to form an annular clearance disposed between the first and second movable members, the annual clearance being in fluid transmitting relationship with the second inflatable member, whereby the second inflatable member may be expanded upon the introduction of fluid into the annular clearance.

2. The catheter of claim 1, wherein the shaft includes a first passage disposed in fluid transmitting relationship with the first inflatable member, whereby the first inflatable member may be expanded upon the introduction of a fluid into the first passage.

3. The catheter of claim 1, wherein the means for adjusting includes a moveable member disposed upon the shaft for movement along the longitudinal axis of the shaft.

4. The catheter of claim 1, wherein the means for adjusting the position, of at least one of the first and second inflatable members along the longitudinal axis of the shaft, adjusts the position of the second inflatable member relative to the first inflatable member.

5. The catheter of claim 4, wherein the first end of the shaft is insertable into the body passageway, the first inflatable member is disposed on the shaft proximate the first end of the shaft, and the means for adjusting includes a moveable member disposed upon the shaft between the first inflatable member and the second end of the shaft, for movement along the longitudinal axis of the shaft.

6. The catheter of claim 5, wherein the second inflatable member is disposed upon the moveable member, whereby upon movement of the moveable member, the location of the second inflatable member may be adjusted with respect to the first inflatable member.

7. The catheter of claim 6, wherein the moveable member includes a second passage disposed in fluid transmitting relationship with the second inflatable member, whereby the second inflatable member may be expanded upon the introduction of a fluid into the second passage.

8. The catheter of claim 1, wherein the adjusting means includes first and second moveable members disposed on the shaft between the first inflatable member and the second end of the shaft, whereby the first and second moveable members are moveable with respect to the shaft along the longitudinal axis of the shaft.

9. The catheter of claim 8, wherein the second inflatable member has first and second ends, the first end being secured to the first moveable member and the second end being secured to the second moveable member, whereby upon movement of the first and second moveable members, the location of the second inflatable member may be adjusted with respect to the first inflatable member.

10. The catheter of claim 8, wherein the second moveable member is associated with the first moveable member by a connection means which connects the first and second moveable members to each other, whereby the first and second moveable members may be moved cooperatively along the longitudinal axis of the shaft.

11. The catheter of claim 1, wherein the first and second inflatable members are first and second inflatable balloons.

12. An adjustable multi-balloon catheter, comprising:
a shaft, having first and second ends, a longitudinal axis extending therebetween, and a plurality of internal passages;
a first inflatable balloon disposed upon the shaft adjacent the first end of the shaft, and disposed in a fluid transmitting relationship with at least one of the internal passages of the shaft;
a first moveable member having first and second ends, and disposed upon the shaft between the first inflatable balloon and the second end of the shaft;
a second moveable member associated with the first moveable member, the first and second moveable members being movable with respect to the shaft along the longitudinal axis of the shaft; and
a second inflatable balloon having first and second ends, the first end of the second balloon being secured to the first moveable member, and the second end of the second balloon being secured to the second moveable member, whereby upon movement of the first and second moveable members, the location of the second balloon with respect to the first balloon may be adjusted.

13. The multi-balloon catheter of claim 12, wherein the first and second moveable members are spaced from each other to form an annular clearance disposed between the first and second moveable members, the annular clearance being in fluid transmitting relationship with the second inflatable balloon.

14. The multi-balloon catheter of claim 13, including inlet openings in fluid transmitting relationship with at least one of the passages and the annular clearance, whereby the first and second balloons may be inflated upon introduction of a fluid into at least one passage and the annular clearance through the inlet openings.

15. The multi-balloon catheter of claim 12, wherein the second moveable member is associated with the first moveable member by a connection means which connects the first and second moveable members to each other.

16. The multi-balloon catheter of claim 12, including at least one radiopaque marker secured to the shaft proximate the first balloon and at least one radiopaque marker secured to the first moveable member proximate the second inflatable balloon.

17. The multi-balloon catheter of claim 12, including an elongate guide member disposed in one of the internal passages of the shaft.

18. The multi-balloon catheter of claim 12, including a third inflatable balloon disposed on the shaft between the first inflatable balloon and the first end of the shaft.

19. An apparatus for repairing a body passageway, comprising:
a catheter, including a shaft having first and second ends and a longitudinal axis extending from the first end to the second end of the shaft, and first and second inflatable members disposed upon the shaft along the longitudinal axis of the shaft;
a first securing means disposed upon the first inflatable member;
a second securing means disposed upon the second inflatable member;
a prosthesis having first and second ends, whereby the first securing means is attached to the prosthesis proximate the first end of the prosthesis and the second securing means is associated with the prosthesis proximate the second end of the prosthesis;
means for inflating the first and second inflatable members; and
means for adjusting the location of the second inflatable member with respect to the first inflatable member along the longitudinal axis of the shaft, whereby the location of the second inflatable member and second securing means may be adjusted with respect to the first inflatable member after the first and second inflatable members have been disposed within the body passageway.

20. The apparatus of claim 19, wherein the first and second securing means are expandable tubular shaped members.

21. The apparatus of claim 19, wherein the first and second inflatable members are first and second inflatable balloons.

22. The apparatus of claim 19, wherein the first end of the shaft is insertable into the body passageway, the first inflatable member is disposed on the shaft proximate to the first end of the shaft, and the means for adjusting includes a moveable member disposed upon the shaft between the first inflatable member and the second end of the shaft, for movement along the longitudinal axis of the shaft.

23. The apparatus of claim 22, wherein the second inflatable member is disposed upon the moveable member, whereby upon movement of the moveable member, the location of the second inflatable member may be adjusted with respect to the first inflatable member.

24. The apparatus of claim 23, wherein the shaft includes a first passage disposed in fluid transmitting relationship with the first inflatable member, and the moveable member includes a second passage disposed in fluid transmitting relationship with the second inflatable member, whereby the first and second inflatable members may be expanded upon the introduction of a fluid into the first and second passages.

25. The apparatus of claim 19, wherein the adjusting means includes first and second moveable members disposed on the shaft between the first inflatable member and the second end of the shaft, whereby the first and second moveable members are moveable with respect to the shaft along the longitudinal axis of the shaft.

26. The apparatus of claim 25, wherein the second inflatable member has first and second ends, the first end being secured to the first moveable member and the second end being secured to the second moveable member, whereby upon movement of the first and second moveable members, the location of the second inflatable member may be adjusted with respect to the first inflatable member.

27. The apparatus of claim 25, wherein the second moveable member is associated with the first moveable member by a connection means which connects the first and second moveable members to each other, whereby the first and second moveable members may be moved cooperatively along the longitudinal axis of the shaft.

28. The apparatus of claim 25, wherein the first and second moveable members are spaced from each other to form an annular clearance disposed between the first and second moveable members, the annular clearance being in fluid transmitting relationship with the second inflatable member, whereby the second inflatable member may be expanded upon the introduction of fluid into the annular clearance.

29. A method, for use with a catheter having at least first and second inflatable portions, for adjusting the position of at least one of the inflatable portions of the catheter while the catheter is located in a body passageway to implant, within the body passageway, a prosthesis, having first and second ends, carried upon the catheter, comprising the steps of:

providing a first securing means for the first end of the prosthesis;

providing the first securing means and the first end of the prosthesis on the first inflatable portion of the catheter;

providing a second securing means on the second inflatable portion of the catheter;

disposing the catheter, first and second securing means and prosthesis within the body passageway;

positioning the first inflatable portion of the catheter, first securing means and first end of the prosthesis within the body passageway at a desired location; and moving the second inflatable portion of the catheter with respect to the first inflatable portion.

30. The method of claim 29, further including the step of inflating the first inflatable portion to expand the first securing means, whereby the first securing means and first end of the prosthesis are secured within the body passageway.

31. The method of claim 29, further including the steps of positioning the second inflatable portion at a desired location within the prosthesis, and inflating the second inflatable portion to expand the second securing means to secure the second securing means and prosthesis within the body passageway.

32. The method of claim 29, further comprising the steps of providing at least one moveable member disposed on the catheter, disposing the second inflatable portion of the catheter onto the at least one moveable member; and positioning the second inflatable portion at a desired location within the body passageway by moving the at least one moveable member relative the first inflatable portion of the catheter after the first inflatable portion is positioned within the body passageway.

33. The method of claim 32, further including the step of inflating the second inflatable member to expand the second securing means to secure the second securing means and prosthesis within the body passageway.

34. The method of claim 33, further including the steps of deflating the first inflatable member, deflating the second inflatable member and removing the catheter from the body passageway.

* * * * *

UNITED STATES PATENT AND TRADEMARK OFFICE
CERTIFICATE OF CORRECTION

PATENT NO : 5,820,595
DATED : October 13, 1998
INVENTOR(S): Parodi

It is certified that error appears in the above-identified patent and that said Letters Patent are hereby corrected as shown below:

Column 10, line 49, delete "annual", and insert --annular--.

Signed and Sealed this

Twenty-third Day of March, 1999

Attest:

Q. TODD DICKINSON

Attesting Officer

Acting Commissioner of Patents and Trademarks